United States Patent [19] [11] 4,082,753
Kornfeld et al. [45] Apr. 4, 1978

[54] PENNICLAVINE ACETONIDE

[75] Inventors: Edmund C. Kornfeld; Nicholas J. Bach, both of Indianapolis, Ind.

[73] Assignee: Eli Lilly and Company, Indianapolis, Ind.

[21] Appl. No.: 807,459

[22] Filed: Jun. 17, 1977

Related U.S. Application Data

[60] Division of Ser. No. 658,439, Feb. 17, 1976, which is a continuation-in-part of Ser. No. 603,408, Aug. 11, 1975, Pat. No. 3,968,112, which is a division of Ser. No. 494,147, Aug. 2, 1974, Pat. No. 3,929,796.

[51] Int. Cl.$^2$ ............................................. C07D 457/10
[52] U.S. Cl. ................................. 260/285.5; 424/261
[58] Field of Search ....................................... 260/285.5

[56] References Cited

U.S. PATENT DOCUMENTS

| 2,809,974 | 10/1957 | Kornfeld et al. | 260/285.5 |
| 3,228,943 | 1/1966 | Bernardi et al. | 260/285.5 |
| 3,228,945 | 1/1966 | Camerino et al. | 260/285.5 |
| 3,704,233 | 11/1972 | Eich et al. | 260/285.5 |
| 3,814,765 | 6/1974 | Bernardi et al. | 260/285.5 |
| 3,879,554 | 4/1975 | Temperilli | 260/285.5 |

OTHER PUBLICATIONS

Yamatodani et al.; Bull. Agr. Chem. Soc. Japan, vol. 20, pp. 95-96, (1956).
Bernardi et al.; IUPAC-9th Symposium Semi-Synthesis of Clavine Alkaloids, (6/74).
Kline et al.; J. Orig. Chem. 25, pp. 142-143, (1960).
Tokuru Yui et al.; Jap. Jour. Pharm., vol. 7, pp. 157-161, (1958).

*Primary Examiner*—Richard J. Gallagher
*Assistant Examiner*—Mary Vaughn
*Attorney, Agent, or Firm*—James L. Rowe; Everet F. Smith

[57] ABSTRACT

Synthesis of penniclavine and of elymoclavine, intermediates useful therein, and novel compounds producible therefrom.

1 Claim, No Drawings

PENNICLAVINE ACETONIDE

CROSS-REFERENCE

This application is a division of our copending application Ser. No. 658,439 filed Feb. 17, 1976, which was a continuation-in-part of our then copending application, Ser. No. 603,408 filed Aug. 11, 1975, now U.S. Pat. No. 3,968,112, issued July 6, 1976, which was a division of our then copending application Ser. No. 494,147 filed Aug. 2, 1974, now U.S. Pat. No. 3,929,796 issued Dec. 30, 1975.

BACKGROUND OF THE INVENTION

Compounds based on the ergoline ring system (I):

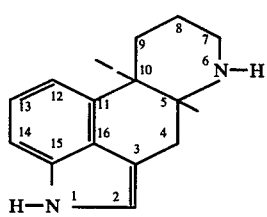

have a surprising variety of pharmaceutical activities. For example, lysergic and isolysergic acid are D-8-carboxy-6-methyl-$\Delta^9$-ergolines (9,10-didehydroergolines or 9-ergolenes.) The amides of lysergic acid have valuable and unique pharmacologic properties, and include the naturally-occurring peptide alkaloids; ergocornine, ergokryptine, ergonovine, ergocristine, ergosine, ergotamine, etc.; synthetic oxytocic alkaloids such as methergine; and the synthetic hallucinogen - lysergic acid diethylamide or LSD. Ergotamine, a 9-ergolene, with a "peptide" side chain, has been used in the treatment of migraine and recently, both ergocornine and 2-bromo-α-ergokryptine have been shown to be inhibitors of prolactin and of dimethylbenzanthracene (DMBA)-induced tumors in rats, according to Nagaswa and Meites, Proc. Soc. Exp'tl. Bio. Med. 135, 469 (1970) and to Heuson et al., Europ. J. Cancer, 353 (1970). (See also U.S. Patents 3,752,888 and 3,752,814).

Non-peptide ergot derivatives, both naturally occurring and totally or partially synthetic, share these multiple pharmacological properties with the peptide derivatives. For example, D-6-methyl-8-cyanomethylergoline, was prepared by Semonsky and co-workers, Coll, Czech. Chem. Commun., 33, 577 (1968), and was found to be useful in preventing pregnancy in rats - Nature, 221, 666 (1969). (See also U.S. Pat. No. 3,732,231) — by interfering with the secretion of hypophysial leuteotropic hormone and the hypophysial gonadotropins or by inhibiting the secretion of prolactin. [See Seda et al., Reprod. Fert., 24, 263 (1971) and Mantle and Finn, id. 441)]. Semonsky and co-workers, Coll, Czech. Chem. Comm., 36, 220 (1971), have also prepared D-6-methyl-8-ergolinylacetamide, a compound which is stated to have anti-fertility and anti-lactating effects in rats. the 2-halo derivatives of D-6-methyl-8-cyanomethylergoline and of D-6-methyl-8-ergolinylacetamide have been prepared and tested for their prolactin inhibiting activity (M. J. Sweeney, J. A. Clemens, E. C. Kornfeld and G. A. Poore, 64th Annual Meeting Amer. Assoc. Cancer Research, April, 1973).

A number of the non-peptide indole alkaloids have been found in fungus cultures grown on Elymus nollis and other related grasses. These non-peptide alkaloids include chanochlavine, agroclavine, elymoclavine, and penniclavine. Of particular interest are agroclavine, an 8-methyl-8-ergolene; elymoclavine, an 8-hydroxymethyl-8-ergolene, and penniclavine, an 8-hydroxymethyl-8-hydroxy-9-ergolene. These non-peptide alkaloids have been shown to have potent rat prolactin inhibiting activity comparable to that found with the peptide alkaloid, ergocornine.

It is an object of this invention to provide a synthesis of penniclavine and of elymoclavine from optically active starting materials. It is a further object of this invention to provide useful penniclavine derivatives. Other objects of this invention will become apparent from the specification which follows.

SUMMARY OF THE INVENTION

In fulfillment of the above and other objects, this invention provides a method of synthesizing penniclavine (structure I below).

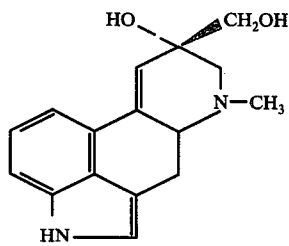

According to this novel synthetic procedure, methyl lysergate (structure II below) is oxidized by the procedure of U.S. Pat. No. 3,814,765 utilizing mercuric acetate in an alkanol followed by a sodium borohydride treatment to provide a 6-methyl-8-carbomethoxy-10α-alkoxy-8-ergolene [III below wherein alk is ($C_1$-$C_3$) alkyl]. (The use of the term "ergolene" comprehends the naturally occurring form derived from D-lysergic acid throughout this specification.) Reduction of the 8-carbomethoxy group with a metal hydride reducing agent yields a 6-methyl-8-hydroxymethyl-10α-alkoxy-8-ergolene [IV below wherein alk is ($C_1$-$C_3$) alkyl]. Treatment of this intermediate 8-hydroxymethyl compound with acid causes an allylic arrangement with the consequent formation of penniclavine (I above and V below wherein R is H).

Carrying out the allylic arrangement of IV in a lower alkanol in the presence of acid yields the lower alkyl ether derivatives of penniclavine, (V wherein R is alk), hitherto unknown. The above synthetic procedure is illustrated in Reaction Sequence 1 below, Reaction Sequence I

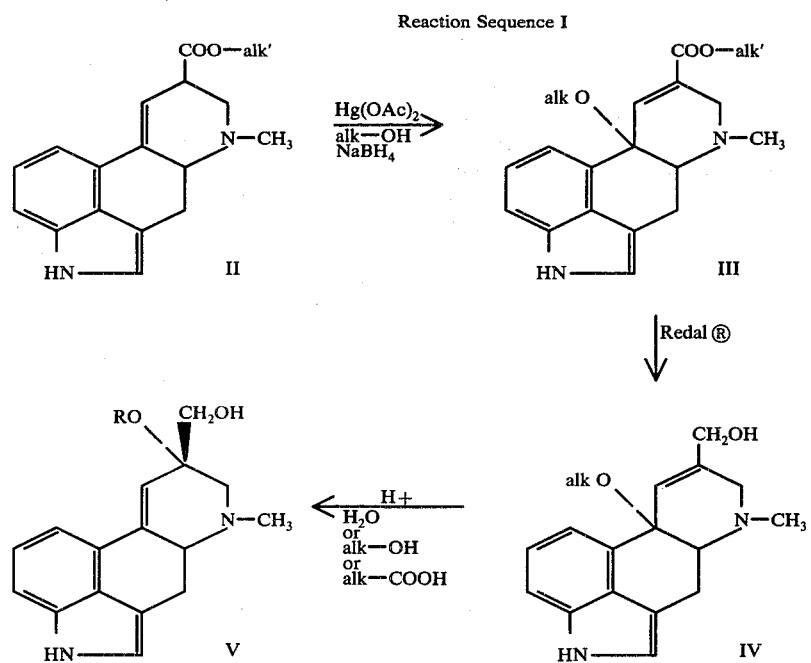

wherein alk and alk' are the same or different ($C_1$–$C_3$) alkyl groups and wherein R is H (penniclavine), alk (penniclavine 8α-ethers) or alk-CO (penniclavine esters).

In Reaction Sequence 1, the reaction going from methyl D-lysergate to the 10α-alkoxy compound (III) is probably an oxidative hydration of the $\Delta^9$ double bond followed by dehydration to produce a $\Delta^8$ double bond. The alkyl group of the 10α-alkoxy radical will be the same as the alkanol employed in the hydration reaction itself. In reducing the carbomethoxy group of III of yield the 8-hydroxymethyl group of IV, the prefered reducing agent is Redal® (sodium bis[2-methoxyethoxy] aluminum hydride). Other hydride reducing agents, however, are fully operative to yield the desired 8-hydroxymethyl group. The allylic arrangement of the 8-hydroxymethyl-10α-alkoxy compound (IV) to yield penniclavine, a penniclavine ether or a penniclavine acylate is carried out under standard allylic rearrangement conditions employing an acid. The medium in which the rearrangement takes place, either aqueous, acidic or alkanolic, in general determines the nature of the C-8 group; that is to say, the predominant species in the solvent will determine the nature of the R radical in V above. For example, if the rearrangement is carried out in ethanol, the product of the reaction will be an 8α-ethoxy compound. Similarly, if the reaction is carried out in a propionic acid medium, the product of the reaction will be an 8α-propionoxy derivative. If a predominantly aqueous medium is used, the reaction product is, of course, penniclavine.

In Reaction Sequence 1, the compounds represented by structures III and IV are novel intermediates useful in the synthesis of penniclavine and the other derivatives represented by structure V. Similarly, the novel compounds represented by structure V (wherein R is alk or alk-CO) are useful in that they can be transformed readily to penniclavine by use of acid hydrolysis in a predominantly aqueous medium. In addition, all of the compounds represented by V, including penniclavine, are prolactin inhibitors.

In an extension of the above synthetic procedure, we have found that treatment of a compound of structure IV with a lower alkyl anhydride such as acetic anhydride, propionic anhydride or butyric anhydride yields the C-8 lower alkyl esters of structure IV as represented by structure VI.

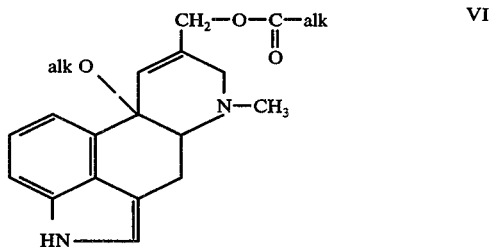

wherein alk is ($C_1$–$C_3$) alkyl. These compounds are also useful intermediates in that they can be transformed to penniclavine or the penniclavine derivatives represented by V rearrangement.

The novel intermediate (IV) above can also be transformed to yield the 10α-alkylmercapto ethers related to penniclavine and represented by VII.

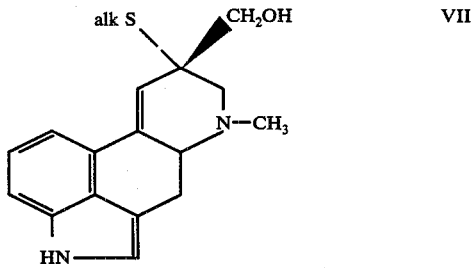

wherein alk is ($C_1$–$C_3$) alkyl. These compounds are prepared by treating our novel intermediate (IV) with an alkylmercaptan (alk-SH) in the presence of a Lewis acid such as borontrifluoride. These 8α-alkylmercapto derivatives are also useful as prolactin inhibitors and as oxytocic agents.

The novel intermediate (IV) can also be transformed by treatment with lithium aluminumhydride followed by treatment with aluminum chloride to yield elymoclavine (structure VIII).

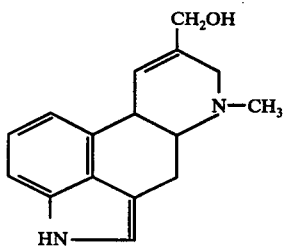

ELYMOCLAVINE

Elymoclavine is also a prolactin inhibitor.

Finally, we have found that penniclavine can be readily transformed to an acetonide represented by structure IX below by treatment with acetone in the presence of acid.

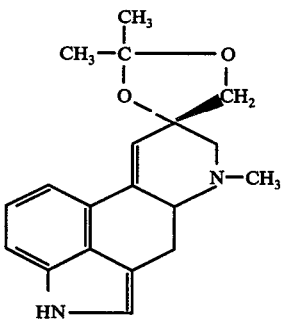

This penniclavine acetonide is also a powerful prolactin inhibitor.

Also included within the scope of this invention are the non-toxic salts of the ergolene bases represented by V above when R is alk or alk-CO, by VII and by IX. These nontoxic salts can be formed with both organic and inorganic pharmaceutically-acceptable acids. Such salts include sulfates, such as sulfate, pyrosulfate, and bisulfate; sulfites, such as sulfite and bisulfite; nitrate; phosphates, such as phosphate, monohydrogenphosphate, dihydrogenphosphate, metaphosphate and pyrophosphate; halides, such as chloride, bromide and iodide; $C_1$–$C_{10}$ aliphatic carboxylates, such as acetate, propionate, decanoate, caprylate, acrylate, formate, isobutyrate, caprate, heptanoate and propiolate; $C_1$–$C_{10}$ aliphatic dicarboxylates, such as oxalate, malonate, succinate, suberate, sebacate, fumarate, maleate, butyne-1,4-dioate and hexyne-1,6-dioate; benzoates, such as benzoate, chlorobenzoate, methylbenzoate, dinitrobenzoate, hydroxybenzoate and methoxybenzoate; phthalates, such as phthalate and terephthalate; arylsulfonates, such as toluenesulfonate and xylenesulfate; citrate; $C_2$–$C_5$ α-hydroxy-alkanoates, such as lactate, α-hydroxybutyrate and glycollate; $C_4$–$C_6$ α-hydroxyalkanedioates, such as malate and tartrate; and $C_1$–$C_3$ alkylsulfonates, such as methanesulfonate and propanesulfonate.

This invention is further illustrated by the following specific examples.

EXAMPLE 1

PREPARATION OF 6-METHYL-8-CARBOMETHOXY-10α-METHOXY-8-ERGOLENE

Following the procedure of U.S. Pat. No. 3,814,765 a solution of 11.2 g. of mercuric acetate in 250 ml. of methanol was added in dropwise fashion over a period of about one hour to a solution of 9.8 g. of methyl D-lysergate in 250 ml. of methanol. After the addition had been completed, the reaction mixture was stirred at room temperature under a nitrogen atmosphere for about 3 hours and was then cooled with an ice-water mixture. The pH of the solution was adjusted to 9.8 with 10 percent aqueous sodium hydroxide. Next, a solution of 2 g. of sodium borohydride in 20 ml. of water was added slowly to the alkaline solution. The reaction mixture was stirred with cooling for about 5 minutes and was then poured onto ice. The aqueous layer was extracted with chloroform. The chloroform layer was separated and extracted with aqueous tartaric acid. The tartaric acid layer, containing 6-methyl-8-carbomethoxy-10α-methoxy-8-ergolene formed in the above reaction as the tartrate salt, was made basic with dilute ammonium hydroxide. The 8-ergolene, being insoluble in basic solution, separated and was extracted with ethyl acetate. The ethyl acetate layer was separated, washed first with water and then with saturated aqueous sodium chloride and dried. Evaporation of the ethyl acetate left as a residue 6-methyl-8-carbomethoxy-10α-methoxy-8-ergolene which was purified by dissolving the residue in chloroform and filtering the chloroform solution through 200 g. of florisil. Evaporation of the chloroform yielded purified 6-methyl-8-carbomethoxy-10α-methoxy-8-ergolene which melted at 179°–180° C. with decomposition after recrystallization from ether.

Analysis Calc.: C, 69.21; H, 6.45; N, 8.97;
Found: C, 69.38; H, 6.21; N, 8.74.

EXAMPLE 2

PREPARATION OF 6-METHYL-8-HYDROXYMETHYL-10α-METHOXY-8-ERGOLENE

A solution was prepared containing 12.8 g. of 6-methyl-8-carbomethoxy-10α-methoxy-8-ergolene in 800 ml. of tetrahydrofuran (THF). 30 ml. of a 70 percent solution of sodium bis (2-methoxyethoxy) aluminum hydride in benzene was added in dropwise fashion. The reaction mixture was stirred at room temperature for about one-half hour and then cooled in an ice-water bath. Excess hydride reducing agent was decomposed by the addition of an ethyl acetate-water mixture. The reaction mixture was diluted with water, and the water layer repeatedly extracted with chloroform until the chloroform extract gave a negative Van Urk test (a color test for indole alkaloids). The chloroform extracts were combined, washed with saturated aqueous sodium chloride and dried. Chloroform was removed by evaporation, and the resulting residue, comprising 6-methyl-8-hydroxymethyl-10α-methoxy-8-ergolene formed in the above reaction, was recrystallized by triturating with ether. 6-Methyl-8-hydroxymethyl-10α-methoxy-8-ergolene thus prepared melted at 216°–18° C. with decomposition after recrystallization from ethyl acetate.

Analysis Calc.: C, 71.81; H, 7.09; N, 9.85;
Found: C, 71.59; H, 6.80; N, 9.85.

EXAMPLE 3

PREPARATION OF 6-METHYL-8-ACETOXYMETHYL-10α-METHOXY-8-ERGOLENE

A solution was prepared containing 2.3 g. of 6-methyl-8-hydroxymethyl-10α-methoxy-8-ergolene in 100 ml. of pyridine. 10 ml. of acetic anhydride were added; the reaction mixture was stirred at room temperature for 1.5 hours and was then poured into an ice-10 percent aqueous ammonium hydroxide mixture. 6-Methyl-8-acetoxymethyl-10α-methoxy-8-ergolene formed in the above reaction was insoluble in the aduous alkaline layer and was extracted with ethyl acetate. The ethyl acetate extract was separated, washed with water followed by saturated aqueous sodium chloride and then dried. Evaporation of the ethyl acetate yielded a residue comprising 6-methyl-8-acetoxymethyl-10α-methoxy-8-ergolene which was crystallized from ether; m.p. = 180° C. with decomposition.

Analysis Calc.: C, 69.92; H, 6.79; N, 8.58;
Found: C, 69.71; H, 6.54; N, 8.39.

EXAMPLE 4

SYNTHESIS OF PENNICLAVINE

A solution was prepared containing 1.94 g. of 6-methyl-8-hydroxymethyl-10α-methoxy-8-ergolene in 250 ml. of 2 percent aqueous tartaric acid. The reaction mixture was kept under a nitrogen atmosphere at room temperature for about 3 days, and was then made basic with 10 percent aqueous ammonium hydroxide. Penniclavine, formed in the above reaction, was insoluble in the alkaline layer and was extracted into chloroform. The chloroform extractions were continued until a negative Van Urk test was obtained. The chloroform extracts were combined, washed with saturated aqueous sodium chloride and dried. Evaporation of the chloroform left as a residue penniclavine which was further purified by dissolution in chloroform and chromatographing the chloroform solution over 190 grams of florisil. The penniclavine was eluted with chloroform containing 3–7 percent methanol. The development of the chromatogram was followed on thin layer chromatography, and fractions shown to contain penniclavine by this technique were combined and the solvent evaporated therefrom to yield penniclavine as a residue. Recrystallization of the penniclavine from chloroform gave crystalline material melting at 212°–214° C.

Analysis Calc.: C, 71.09; H, 6.71; N, 10.36;
Found: C, 70.85; H, 6.44; N, 10.08.

EXAMPLE 5

PREPARATION OF 6-METHYL-8β-HYDROXYMETHYL-8α-ACETOXY-9-ERGOLENE

A solution of 535 mg. of 6-methyl-8-hydroxymethyl-10α-methoxy-8-ergolene in 50 ml. of acetic acid was prepared, and the solution stirred at room temperature under a nitrogen atmosphere for 1 hour. The reaction mixture was then poured onto ice, and the resulting aqueous solution made basic with dilute ammonium hydroxide. Extraction of the alkaline layer with chloroform was continued until a negative Van Urk test was obtained. The chloroform extracts were combined, washed with saturated aqueous sodium chloride and dried. Evaporation of the chloroform yielded a residue which was redissolved in chloroform and the chloroform solution chromatographed over florisil using chloroform containing 1 percent methanol as the eluant. Fractions shown by thin layer chromatography to contain 6-methyl-8β-hydroxymethyl-8α-actoxy-9-ergolene formed in the above reaction were combined, the solvent evaporated therefrom, and the residue recrystallized from ethanol. 6-Methyl-8β-hydroxymethyl-8α-acetoxy-9-ergolene thus purified melted at 154°–5° C. with decomposition.

Analysis Calc.: C, 69.21; H, 6.45; N, 8.97;
Found: C, 69.49; H, 6.35; N, 8.86.

EXAMPLE 6

PREPARATION OF 6-METHYL-8β-HYDROXYMETHYL-8α-METHOXY-9-ERGOLENE

A solution was prepared containing 525 mg. of 6-methyl-8-hydroxymethyl-10α-methoxy-8-ergolene in 100 ml. of methanol. 1 ml. of borontrifluoride etherate was added. The reaction mixture was stoppered, stirred at room temperature for 60 minutes, and then poured over ice. The resulting aqueous solution was made basic with dilute ammonium hydroxide. The basic layer was extracted with chloroform until a chloroform extract showed a negative Van Urk test. The chloroform extracts were combined, washed with saturated aqueous sodium chloride and dried. Evaporation of the chloroform yielded a residue comprising 6-methyl-8β-hydroxymethyl-8α-methoxy-9-ergolene formed in the above reaction. The residue was dissolved in a chloroform-methanol solution, and the solution chromatographed over 25 g. of florisil using chloroform containing 2 percent methanol as an eluant. Fractions containing 6-methyl-8β-hydroxymethyl-8α-methoxy-9-ergolene, as shown by thin layer chromatography, were combined and recrystallized from methanol; m.p. = 200° C. with decomposition.

Analysis Calc.: C, 71.81; H, 7.09; N, 9.85;
Found: C, 71.62; N, 6.90; N, 9.67.

EXAMPLE 7

PREPARATION OF 6-METHYL-8β-HYDROXYMETHYL-8α-ETHOXY-9-ERGOLENE

A solution was prepared containing 275 mg. of 6-methyl-8-hydroxymethyl-10α-methoxy-8-ergolene in 100 ml. of anhydrous ethanol. 0.1 ml of a 70 percent aqueous perchloric acid was added, and the reaction mixture stirred at room temperature for 100 minutes. The reaction mixture was poured over ice, the resulting aqueous layer made basic with dilute ammonium hydroxide, and the alkaline layer extracted with chloroform until a chloroform extract showed a negative Van Urk test. The chloroform extracts were combined, washed with saturated sodium chloride, dried and the chloroform evaporated therefrom Chromatography of the resulting residue, containing 6-methyl-8β-hydroxymethyl-8α-ethoxy-9-ergolene formed in the above reaction, over florisil using chloroform with 1-5 percent methanol as an eluant yielded purified material melting at 133°–4° C. with decomposition.

Analysis Calc.: C, 72.46; H, 7.43; N, 9.39; Found: C, 72.64; H, 7.28; N, 9.52.

EXAMPLE 8

PREPARATION OF 6-METHYL-8β-HYDROXYMETHYL-8α-METHYLMERCAPTO-9-ERGOLENE

A solution containing 525 mg. of 6-methyl-8-hydroxymethyl-10α-methoxy-8-ergolene in 25 g. of methylmercaptan was stirred for one-half hour at 0°–10° C. One milliliter of borontrifluoride etherate was added, and the stirring continued at the same temperature for an additional hour. At this point, all the ingredients were not in solution, and 25 ml. of tetrahydrofuran were added. The reaction mixture was stirred for an additional hour and then diluted with water. The resulting aqueous layer was made basic with dilute ammonium hydroxide, and the alkaline layer extracted with chloroform until an extract showed a negative Van Urk test. The chloroform extracts were combined and washed with saturated aqueous sodium chloride. The chloroform was evaporated. The resulting residue was redissolved in chloroform and chromatographed over florisil using chloroform containing 0–1 percent methanol as the eluant. Fractions shown by thin layer chromatography to contain 6-methyl-8β-hydroxymethyl-8α-methylmercapto-9-ergolene prepared in the above reaction were combined and recrystallized from ether; m.p. = 160°–2° C. with decomposition.

Analysis Calc.: C, 67.97; H, 6.76; N, 9.32; S, 10.67; Found: C, 68.08; H, 6.83; N, 9.07; S, 10.92.

Earlier fractions were shown by thin layer chromatography to contain both 6-methyl-8β-hydroxymethyl-8α-methylmercapto-9-ergolene and its 8α-hydroxymethyl-8β-methylmercapto isomer. This latter compound is slightly less polar than 6-methyl-8α-hydroxymethyl-8β-methylmercapto-9-ergolene, and the mixture can be separated by chromatography.

EXAMPLE 9

PREPARATION OF PENNICLAVINE ACETONIDE

A solution was prepared containing 290 mg. of penniclavine in 150 ml. of acetone. 0.3 ml. of 70 percent aqueous perchloric acid were added; the reaction mixture was stoppered and stirred at room temperature for about 2 hours, and was then poured into aqueous ammonium hydroxide. The organic material was extracted from the alkaline layer with ethyl acetate. The ethyl acetate layer was separated, washed with water and with saturated aqueous sodium chloride and then dried. Evaporation of the organic solvent yielded a residue comprising penniclavine acetonide formed in the above reaction. The residue was dissolved in chloroform and chromatographed over florisil using chloroform containing 2 percent ethanol as the eluant. Fractions shown to contain penniclavine acetonide by thin layer chromatography were combined and recrystallized from ethanol. Penniclavine acetonide thus prepared melted at 260° C. with decomposition.

Analysis Calc.: C, 73.52; H, 7.14; N, 9.03; Found: C, 73.23; H, 6.91; N, 8.80.

EXAMPLE 10

SYNTHESIS OF ELYMOCLAVINE

A solution was prepared containing 865 mg. of 6-methyl-8-hydroxymethyl-10α-methoxy-8-ergolene in 150 ml. of tetrahydrofuran (THF). 1 g. of lithium aluminumhydride was added thereto in portions. After the addition had been completed, the reaction mixture was stirred at room temperature under a nitrogen atmosphere for one hour. Next, a solution of 1 g. of aluminum chloride in 50 ml. of THF was added in dropwise fashion. Again, after the addition had been completed, the reaction mixture was diluted with water, and the aqueous layer extracted with chloroform until a chloroform extract showed a negative Van Urk test. The chloroform extracts were combined, washed with saturated sodium chloride and dried, and the solvent evaporated. Recrystallization of the resulting residue from methanol yielded a mixture of elymoclavine and lysergol, separable by chromatography.

As previously stated, the 9-ergolenes of this invention represented by V above wherein R is alk or alk-CO-, by VII and by IX are useful as prolactin inhibitors. The inhibition of prolactin secretion by the compounds of this invention is evidenced by the following experiment: Adult male rats of the Sprague-Dawley strain weighing about 200 g. were used. All rats were housed in an air-conditioned room with controlled lighting (lights on 6 a.m. – 8 p.m.) and fed lab chow and water *ad libitum*.

In each experiment the rats were killed by decapitation, and 150 μl aliquots of serum were assayed for prolactin. Each male rat received an intraperitoneal injection of 2.0 mg of reserpine in aqueous suspension 18 hours before administration of the ergoline derivative. The purpose of the reserpine was to keep prolactin levels uniformly elevated. The derivatives were dissolved in 10% ethanol at a concentration of 10 mcg/ml, and were injected intraperitoneally at a standard dose of 50 mcg/kg. Each compound was administered to a group of 10 rats, and a control group of 10 intact males received an equivalent amount of 10 percent ethanol. One hour after treatment all rats were killed by decapitation, and the serum was collected and assayed for prolactin as previously described. The results were evaluated statistically using Student's "$t$" test to calculate the level of significance, "$p$".

The difference between the prolactin level of the treated rats and prolactin level of the control rats, divided by the prolactin level of the control rats gives the percent inhibition of prolactin secretion attributable to the compounds of this invention. The table which follows gives prolactin inhibition percentages for a series of 9-ergolenes of this invention. In the table, column 1 gives the name of the compound; column 2, the dose level of the compound in the prolactin inhibition test; column 3, the percent prolactin inhibition; and column 4, the level of significance.

Table

| Name of Compound | Dose | % Prolactin Inhibition | "$p$" Value |
| --- | --- | --- | --- |
| 6-methyl-8β-hydroxymethyl-8α-ethoxy-9-ergolene | 10 mcg | 36 | < .01 |
| penniclavine acetonide | 10 mcg | 56 | <.001 |
| 6-methyl-8β-hydroxymethyl-8α-methoxy-9-ergolene | 10 mcg | 44 | < .01 |

In the same test, penniclavine at a 10 mcg. level gave 40 percent inhibition, and elymoclavine at a 10 mcg. level, 71 percent inhibition. An intermediate compound of structure III, the 10α-methoxy derivative, was also active as a prolactin inhibitor with a 27 percent inhibition at a 10 mcg. dose level.

As prolactin inhibitors, the 9-ergolenes of this invention are useful in the treatment of inappropriate lactation such as postpartum lactation and galactorrhea. In addition, the compounds can be used to treat prolactin-dependent adenocarcinomas and prolactin-secreting pituitary tumors as well as the following disorders: Forbes - Albright syndrome, Chiari - Frommel syndrome, gynecomastia itself and gynecomastia occurring as a result of estrogenic steroid administration for prostatic hypertrophy, fibrocystic disease of the breast (benign nodules), prophylactic treatment of breast cancer, and breast development resulting from the administration of psychotropic drugs, for example, thorazine, or for prostatic hypertrophy itself.

In carrying out my novel control method, using the compounds of this invention to inhibit prolactin secretion, a 9-ergolene or a salt thereof with a pharmaceutically-acceptable acid is suspended in corn oil and the suspension injected parenterally or fed to a female mammal in amounts varying from 0.01 to 10 mg/kg/day of mammalain weight. Oral administration is preferred. If parenteral administration is used, the injection is preferably by the subcutaneous route using an appropriate pharmaceutical formulation although other modes of parenteral administration such as intraperitoneal, intramuscular, or intravenous routes are equally effective. In particular, with intravenous or intramuscular administration, a soluble pharmaceutically-acceptable salt of a 9-ergolene, preferably the methanesulfonate or maleate salt, is customarily employed. For oral administration, the compound either as the free base or in the form of a salt thereof can also be mixed with standard pharmaceutical excipients and loaded into empty telescoping gelatin capsules or pressed into tablets.

We claim:

1. Penniclavine acetonide.

* * * * *